United States Patent
Boday et al.

(10) Patent No.: US 8,796,642 B2
(45) Date of Patent: Aug. 5, 2014

(54) CARBON NANOTUBES WITH FLUORESCENT SURFACTANT

(71) Applicant: International Business Machines Corporation, Armonk, NY (US)

(72) Inventors: Dylan J. Boday, Tucson, AZ (US); Joseph Kuczynski, Rochester, MN (US); Jason T. Wertz, Wappingers Falls, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 51 days.

(21) Appl. No.: 13/688,488

(22) Filed: Nov. 29, 2012

(65) Prior Publication Data
US 2014/0145094 A1   May 29, 2014

(51) Int. Cl.
*G01N 21/64* (2006.01)
*B82Y 40/00* (2011.01)

(52) U.S. Cl.
CPC ............... *G01N 21/64* (2013.01); *B82Y 40/00* (2013.01); *G01N 21/6428* (2013.01)
USPC ..................................................... 250/459.1

(58) Field of Classification Search
CPC ............... B82Y 40/00; C01B 2202/02; G01N 21/6428; G01N 21/64
USPC ..................................................... 250/459.1
See application file for complete search history.

(56) References Cited

U.S. PATENT DOCUMENTS

| | | | |
|---|---|---|---|
| 7,682,523 B2 | 3/2010 | Weisman et al. | |
| 7,744,844 B2 | 6/2010 | Barrera et al. | |
| 7,922,936 B2 | 4/2011 | Hampden-Smith et al. | |
| 7,972,426 B2 | 7/2011 | Hinch et al. | |
| 7,995,196 B1 | 8/2011 | Fraser | |
| 2004/0171175 A1* | 9/2004 | Swanson et al. | 436/518 |
| 2007/0062411 A1* | 3/2007 | Weisman et al. | 106/31.15 |
| 2008/0044651 A1* | 2/2008 | Douglas | 428/339 |
| 2010/0038597 A1 | 2/2010 | Reynolds et al. | |
| 2010/0062194 A1 | 3/2010 | Sun | |
| 2010/0209632 A1* | 8/2010 | Weisman et al. | 428/29 |
| 2011/0210282 A1 | 9/2011 | Foley | |

OTHER PUBLICATIONS

Vaisman et al., "The Roles of Surfactants in Dispersion of Carbon Nanotubes", Advances in Colloid and Interface Science 128-130 (2006) 34-46. Available online Jan. 10, 2007. © 2006 Elsevier B.V. DOI: 10.1016/j.cis.2006.11.007.

* cited by examiner

*Primary Examiner* — Marcus Taningco
(74) *Attorney, Agent, or Firm* — Richard A. Wilhelm; Robert Williams

(57) ABSTRACT

A fluorescent material may include a medium, carbon nanotubes dispersed in the medium, and a fluorescent surfactant. The fluorescent surfactant may be adsorbed to a surface of some of the carbon nanotubes in a concentration sufficient to make the material fluoresce in the presence of radiation. The material may be applied to a material and tested for fluorescence, electrical conductivity, or carbon nanotube structure.

19 Claims, 3 Drawing Sheets

CARBON NANOTUBES WITH FLUORESCENT SURFACTANT

TECHNICAL FIELD

This disclosure is generally directed to carbon nanotubes having a fluorescent surfactant adsorbed to their surface.

BACKGROUND

Carbon nanotubes are cylindrical nanostructures containing carbon atoms in a hexagonal arrangement primarily through $sp^2$ bonds. They can be created by a number of techniques, including chemical vapor deposition, arc discharge, and laser ablation. Carbon nanotubes have generally inert surfaces. Their surfaces may be covalently modified, which may change the electrical and fluorescent properties of the carbon nanotubes.

SUMMARY

In an embodiment of the invention, a fluorescent material includes a medium, carbon nanotubes dispersed in the medium, and a fluorescent surfactant. The fluorescent surfactant is adsorbed to a surface of some of the carbon nanotubes in a concentration sufficient to make the material fluoresce in the presence of radiation.

In another embodiment of the invention, a method for producing a fluorescent material includes dispersing carbon nanotubes and a fluorescent surfactant in a medium and adsorbing the fluorescent surfactant to a surface of the carbon nanotubes in a concentration sufficient to make the material fluoresce in the presence of radiation In another embodiment of the invention, a method for verifying the authenticity of a product having a material includes exposing the material to incident radiation and detecting emissive radiation having a first emission wavelength to verify the authenticity of the product. The material includes a medium, carbon nanotubes dispersed in the medium, and a fluorescent surfactant adsorbed to a quantity of the carbon nanotubes in a concentration sufficient to make the material fluoresce at the emission wavelength in the presence of radiation.

BRIEF DESCRIPTION OF THE DRAWINGS

The drawings illustrate embodiments of the present invention and, along with the description, serve to explain the principles of the invention. The drawings are only illustrative of typical embodiments of the invention and do not limit the invention.

DETAILED DESCRIPTION

Figure 1:
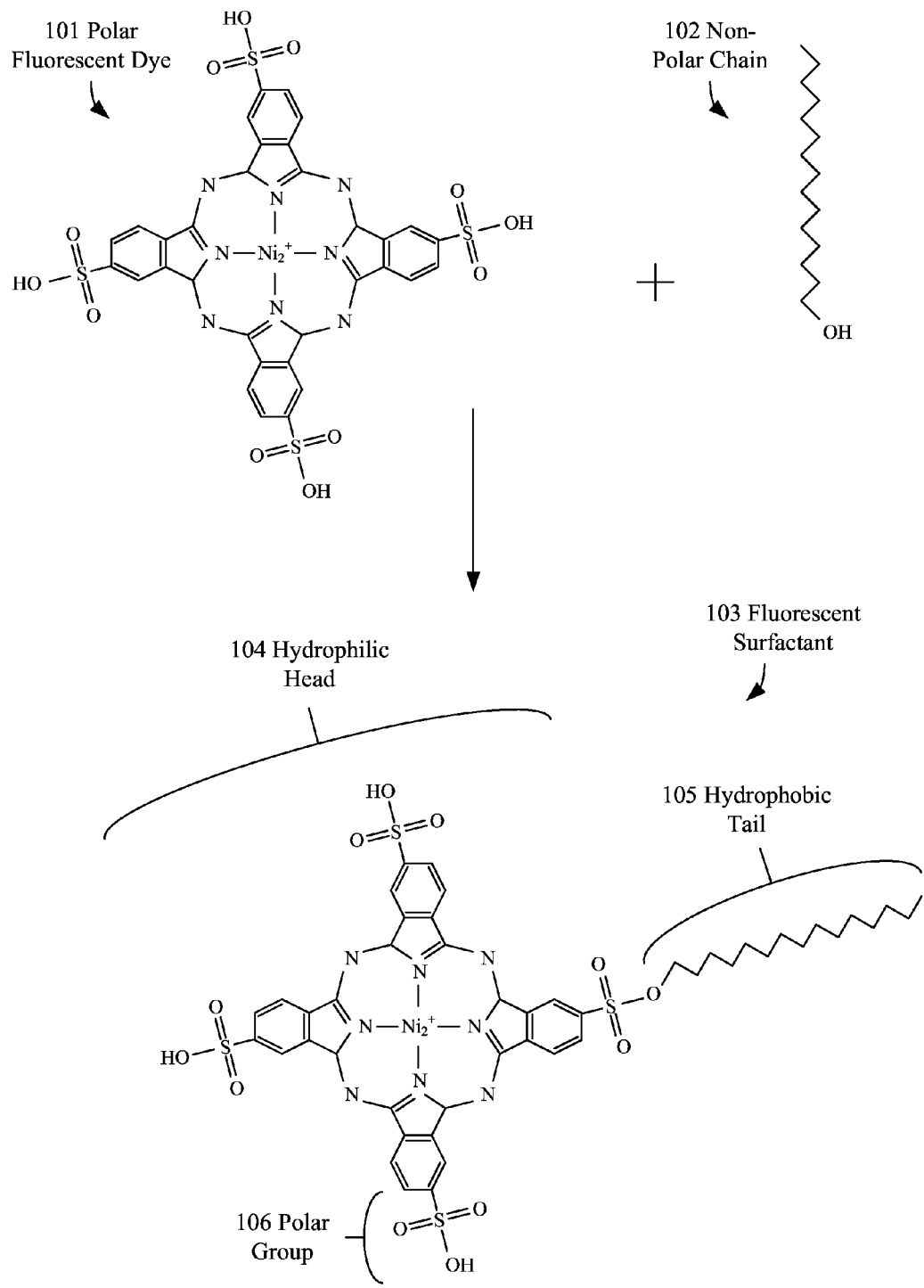
FIG. 1 is a diagrammatic representation of a surfactant molecule, according to embodiments of the invention.

This disclosure is directed toward carbon nanotubes coated with a fluorescent surfactant. The fluorescent surfactant may be adsorbed onto the surfaces of the carbon nanotubes and the coated carbon nanotubes may be dispersed into a medium to form a material. This material may be fluorescent and electrically conductive. The fluorescent surfactant increases the solubility of the carbon nanotubes in the material without modifying the sidewalls of the carbon nanotubes for fluorescent and dispersive functionality.

Carbon nanotubes have valuable intrinsic properties, such as fluorescence, electrical conductivity, and thermal conductivity. These properties make them useful when dispersed into a material. However, carbon nanotubes are generally insoluble due to their tendency to agglomerate and their inert surfaces, and this insolubility affects the electrical conductivity of a material in which the carbon nanotubes are dispersed. Covalent methods of functionalization may increase the dispersive character of the carbon nanotubes, but such methods may modify the structure of the carbon nanotubes, which may adversely affect the carbon nanotubes' properties. Further, the carbon nanotubes' intrinsic fluorescence emission wavelengths and intensity are dependent on the structure and condition of the carbon nanotubes such as agglomeration and surface charge, which are difficult to control. Adsorbing a fluorescent surfactant to the carbon nanotubes may reduce the agglomeration of the carbon nanotubes and increase their solubility in media. Additionally, the fluorescent surfactant may be a fluorescent dye selected for specific fluorescent emission wavelengths and intensities, allowing the fluorescence of a material containing the carbon nanotubes to be controlled and customized.

A material containing dispersed carbon nanotubes having an adsorbed fluorescent surfactant may be electrically conductive and may fluoresce outside the range of the carbon nanotubes. These properties may be especially valuable in applications that require materials to have specific and identifiable properties, such as anti-counterfeiting. The structure of the carbon nanotubes, the electrical conductivity of the material, and the fluorescence of the carbon nanotubes and fluorescent surfactant may not be readily apparent without using an instrument. By painting or imbuing an item with a material that includes a specific fluorescent emission wavelength and intensity, a specific electrical resistance, and/or a specific structure, the item may be uniquely marked and identified.

Surfactant

According to embodiments of the invention, a fluorescent surfactant is adsorbed onto the surfaces of carbon nanotubes. Surfactant molecules are generally amphiphiles, having a polar section and a non-polar section. A fluorescent surfactant may include a hydrophilic fluorescent head (the polar section) and a hydrophobic tail (the non-polar section). The fluorescent surfactant may be produced by reacting a polar fluorescent dye and a non-polar molecular chain, such as through esterification of a functionalized fluorescent dye and a hydrocarbon.

FIG. 1 is a diagrammatic representation of a surfactant molecule, according to embodiments of the invention. A non-polar chain 102, in this case 1-octadecanol, and a polar fluorescent dye 101, in this case phthalocyanine-tetrasulfonic acid nickel(II) complex tetrasodium salt, may be put into solution and reacted, alkylating the polar fluorescent dye 101. The resulting fluorescent surfactant 103, includes a phthlocyanine hydrophilic fluorescent head 104 having sulfonate polar groups 106 and a hydrocarbon hydrophobic tail 105.

According to embodiments of the invention, the fluorescent surfactant may be selected for its fluorescent properties, including its emission wavelength and intensity. The hydrophilic fluorescent head of the fluorescent surfactant may be a fluorescent dye. Fluorescent dyes that may be used include, but are not limited to, xanthene dyes such as rhodamine and fluorescein dyes, oxazine dyes, cyanine dyes, and phthalocyanine dyes. A fluorescent dye may first be functionalized before attaching a hydrophobic tail; for example, if a rhodamine dye is used in the surfactant, it may be functionalized with a sulfonate compound to create sulforhodamine 101 before attaching a hydrocarbon tail. More than one type of fluorescent surfactant may be used depending on the material's desired fluorescent properties, as it may be desirable to test the fluorescent material at multiple wavelengths to increase the level of security of a product with the fluorescent material applied to its surface.

According to embodiments of the invention, the fluorescent surfactant may be selected for the physiochemical properties of its fluorescent hydrophilic head and hydrophobic tail. Many of the physiochemical properties can be varied to achieve the desired dispersive character of the surfactant for different media. Considerations for the fluorescent surfactant's polar properties include the characteristics of a medium in which the surfactant-coated carbon nanotubes may be dispersed and the charge or lack of charge of the surfaces of the carbon nanotubes when present in a medium. The medium in which the fluorescent surfactant and carbon nanotubes are dispersed may have properties that make one type of surfactant better for dispersing the carbon nanotubes. For example, if the medium is a polar medium, it may be desirable to use a cationic fluorescent surfactant. Additionally, when carbon nanotubes are dispersed in a medium, the surfaces of the carbon nanotube may pick up a surface charge. More than one type of fluorescent surfactant may be used, based on the surfactants' polar properties. For example, it may be desired to combine a cationic surfactant and a non-ionic surfactant.

The fluorescent hydrophilic head may be cationic, anionic, non-ionic, or zwitterionic. Physiochemical properties of the fluorescent hydrophilic head include the polar group of the head, the size of the head, and the relative size of the head to the tail. The fluorescent surfactant may have a hydrophobic tail comprising a molecular chain. Molecular chains that may be used include, but are not limited to, hydrocarbons, fluorocarbons, and siloxanes. The hydrophobic tail(s) may be linear, branched, or aromatic. Physiochemical properties of the hydrophobic tail include the length of the tail, the number of tails, and the degree of branching or aromatic character of the tail.

Adsorption and Dispersion

According to embodiments of the invention, the fluorescent surfactant molecules may be adsorbed onto the surfaces of carbon nanotubes. Carbon nanotubes are cylindrical nanostructures containing carbon atoms in a hexagonal arrangement primarily through $sp^2$ bonds. Carbon nanotubes may be functionalized for attachment of moieties; however, functionalization may change the properties of the carbon nanotubes and may require extra steps. Non-covalent surfactant treatment of the carbon nanotubes may preserve the $sp^2$ bond structure of the carbon nanotubes and allow the carbon nanotubes to be dispersed into aqueous or organic solutions. The hydrophobic tail of the fluorescent surfactant may adsorb to the inert external surfaces of the carbon nanotubes through van der Waals attraction or other hydrophobic interactions to create surfactant-coated carbon nanotubes. Alternatively, if the carbon nanotubes are dispersed in a solution and have a surface charge due to the polarity of the solution, the hydrophilic head of the surfactant may adsorb to the charged surfaces of the carbon nanotubes.

Figure 2:
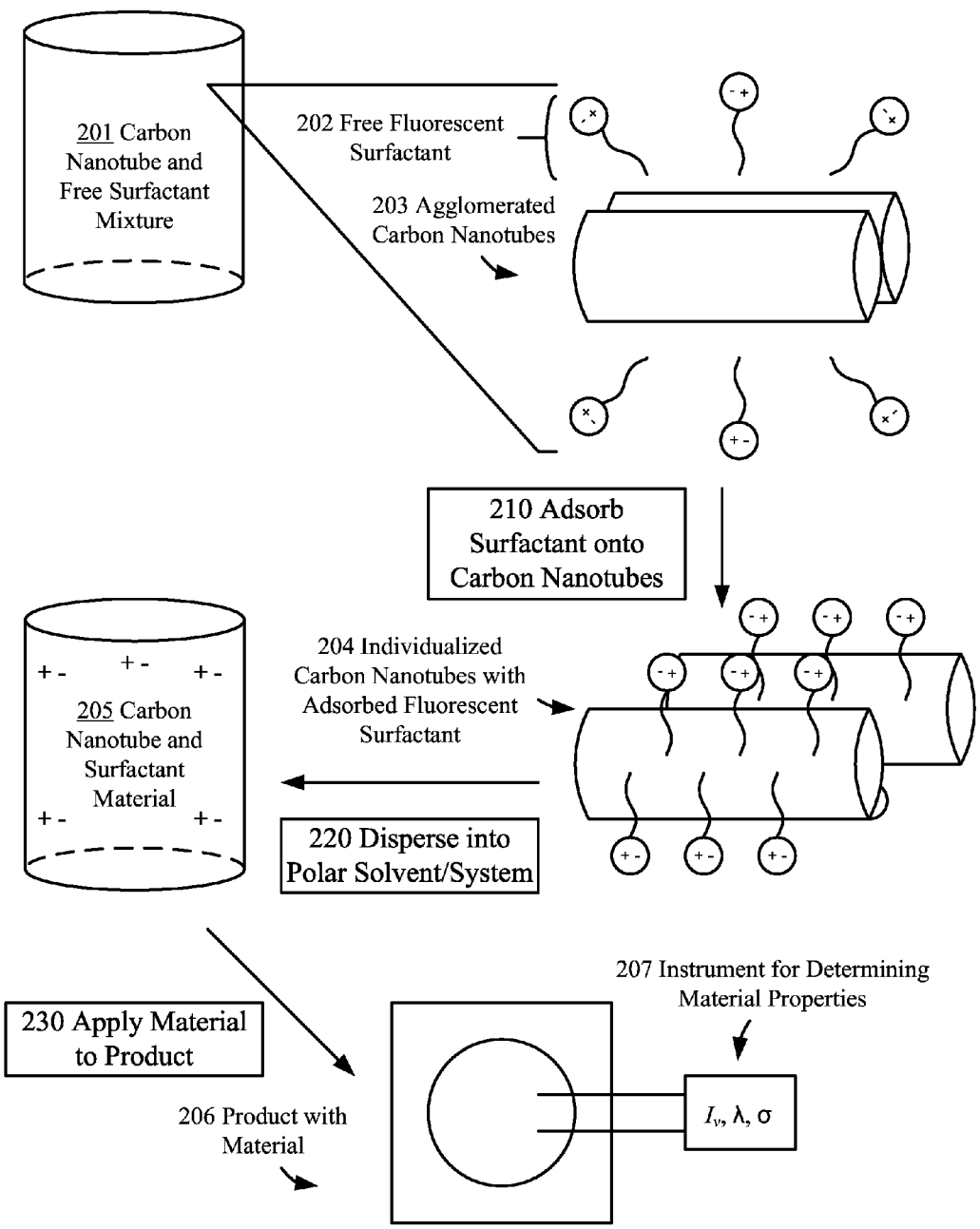
FIG. 2 is a diagrammatic representation of a process to adsorb fluorescent surfactant onto carbon nanotubes and disperse the carbon nanotubes into a material, according to embodiments of the invention.

FIG. 2 is a diagrammatic representation of a process to adsorb fluorescent surfactant onto carbon nanotubes and disperse the carbon nanotubes into a material, according to embodiments of the invention. FIG. 2 is only conceptual, and does not imply the actual orientation of the surfactant or level of dispersion. A mixture 201 includes free fluorescent surfactant 202 and agglomerated carbon nanotubes 203. The free surfactant 202 is adsorbed onto the carbon nanotubes 210. This may be done through first sonicating the agglomerated carbon nanotubes 203 to break them up so that the free surfactant 202 may adsorb onto them. The individualized carbon nanotubes with adsorbed fluorescent surfactant 204 may be dispersed into a polar solvent or system 220, such as a paint or ink. The resulting carbon nanotube and surfactant material 205 may be applied to a product 230, and the product with the material 206 may be tested with an instrument for determining the material's properties 207. Such properties may include fluorescence emission wavelength, fluorescence intensity, conductivity/resistivity, or nanotube structure.

According to embodiments of the invention, the surfactant-coated carbon nanotubes may be dispersed into a polar medium. Untreated carbon nanotubes disperse poorly in solutions due to aggregation of the carbon nanotubes into bundles through van der Waals attractions, and disperse especially poorly in aqueous solutions due to the non-polarity of the carbon nanotubes. Surfactant-coated carbon nanotubes may disperse in solution due to disaggregation of the carbon nanotubes and stability of the dispersion. The surfactant molecules may isolate the carbon nanotubes from each other by adsorbing to the surfaces of the carbon nanotubes so that the carbon nanotubes separate into the solution and do not reaggregate. For example, if the surfactant-coated carbon nanotubes are to be used in a water-based paint, the surfactant-coated carbon nanotubes may be dispersed in an aqueous solution.

According to embodiments of the invention, the fluorescent surfactant is present on the carbon nanotubes in the material above the critical micelle concentration. The surfactant molecules may form micelles with the carbon nanotubes if the concentration of the free surfactant in the solution is above the critical micelle concentration. The critical micelle concentration of the surfactant is the concentration of surfactant at which micelles form. Up until the critical micelle concentration, surfactant molecules added to a solution tend to exist as free molecules that may adsorb onto surfaces; above the critical micelle concentration, surfactant molecules added to a solution tend to form micelles that may form around surfaces.

Carbon nanotubes can exhibit electrical conductivity, and a material with a carbon nanotube concentration above that material's electrical percolation threshold may conduct electricity. When electrically conductive particles are dispersed into a medium, they may form a material with a conducting network. The electrically conductive particles may be dispersed in a high enough concentration for the material to conduct electricity. This concentration is known as the electrical percolation threshold and is influenced by factors such as the medium in which the particles are dispersed, the temperature of the material, and the dispersion of the particles in the medium. Generally, as the weight fraction of the substance in the material or the temperature of the material increases, or as agglomeration of the particles decreases, the electrical percolation threshold decreases. In an embodiment, a material containing fluorescent surface-modified carbon nanotubes may be electrically conductive at or above the electrical percolation threshold. When carbon nanotubes are dispersed into a medium, the resulting material exhibits an electrical percolation threshold, as described above. The conductivity of the material will depend on the characteristics of the medium into which the nanotubes are dispersed and the concentration of nanotubes in the material.

Anti-Counterfeiting

According to embodiments of the invention, a material may be: an ink or a paint that is applied or used to coat all or a portion of a surface of any product; a substance used to make all or part of any product; or a constituent element of the substance used to make all or part of any product. For example, a product may include a part made from a substance that includes the material dispersed in that substance. Moreover, the material may be used in or on packaging or a tag attached to or surrounding any product. A "product" may be any suitable product.

In one embodiment, a material may contain carbon nanotubes with one type of fluorescent surfactant adsorbed to the surface, which may be referred to as a first fluorescent surfactant. The first fluorescent surfactant may have an emission wavelength in or below the visible spectrum (less than 780 nm). For example, in one embodiment, the first fluorescent surfactant may have an emission wavelength of less than 750 nm. In an alternative embodiment, a material may contain carbon nanotubes with two or more fluorescent surfactants adsorbed to the surface, wherein the surfactants have different emission wavelengths in or below the visible spectrum. For example, a first fluorescent surfactant may have an excitation wavelength around 350 nm and an emission wavelength around 400 nm, while a second fluorescent surfactant may have an excitation wavelength around 550 nm and an emission wavelength around 600 nm. The paint may be applied to a product. In one embodiment, the product may be irradiated with radiation at a wavelength of 350 nm to check for fluorescence at 400 nm. In the alternative embodiment, the product may be irradiated with radiation of a wavelength of 350 nm to check for fluorescence at 400 nm, and another light at 550 nm to check for fluorescence at 600 nm. If fluorescence is verified for both light sources, then the product may be verified as authentic. If fluorescence isn't present at both wavelengths, the product may be identified as counterfeit. A counterfeiter must know to check a product for fluorescence, and must also know to check at multiple wavelengths.

In another embodiment of the invention, carbon nanotubes may be dispersed in a material in a concentration and level of dispersion so as to make the material electrically conductive with a particular conductance or at a particular resistance. In one embodiment, the material may be an ink or paint. The dispersion of carbon nanotubes in a material in sufficient concentration to make the material electrically conductive may be in addition to or as alternative to other embodiments described in this description, e.g., the absorption of fluorescent surfactant or inspection of carbon nanotube shape or size using electron microscopy. As discussed earlier, conductivity is dependent on the properties of the material and the concentration of carbon nanotubes within the material, and can be graphed, calculated, or tested with respect to concentration for determination of a predetermined resistance.

The material may be applied to a product such as an ink, paint, or coating. The coated portion of the product will have the particular conductance or resistance. To determine if a product is authentic, a current may be applied to a material and a voltage measured. Alternatively, a voltage may be applied to the material and a current measured. In one alternative, a specific portion of a product may be made from the material. The specific portion of the product made from the material will have the particular conductance or resistance. The resistance of the coated or specific portion may be measured to determine the authenticity of the product. A counterfeiter may not be aware of this electrical property or may not be able to replicate it.

In another embodiment, the authenticity of a product may be determined by examining the product using alternative microscopic techniques, such as electron microscopy. Material having carbon nanotubes may be applied to a product as an ink, paint, or coating. Moreover, the substance from which any part of the product is made may include the material having carbon nanotubes according to the principles of the invention. The region of the product where the material is painted or coated may be examined with an electron microscope. Similarly, a part of the product that is made from a substance that includes the material may be examined with an electron microscope. Inspection with an electron microscope allows a structural characteristic such as the size or shape of the carbon nanotubes to be examined. For example, the process of forming or cutting the nanotubes may be controlled in order to create nanotubes of a certain homogeneous size or shape, such as through chemical vapor deposition. To test for product authenticity, the size or shape of the carbon nanotubes in a material may be inspected and compared with the "controlled for" size or shape of the carbon nanotubes. For particularly expensive or unique products, a counterfeiter may determine the proper emission wavelengths for the fluorescent surfactant and the predetermined electrical resistance for the nanotubes, and apply them to the counterfeit product, but might not properly determine the size or physical structure of the nanotubes. The inspection of carbon nanotube shape or size using electron microscopy may be in addition to or as alternative to other embodiments described in this description, e.g., the attachment of fluorescent surfactant or the dispersion of carbon nanotubes in a material in sufficient concentration to make the material electrically conductive.

These different levels of security can be tailored to an anti-counterfeit system according to the needs of the business and characteristics of the product. For selected items, based on the items' cost, importance, or other distinguishing factor, a system can be tailored to test for fluorescence at multiple wavelengths as well as test for electrical conductivity at specific resistances. For more expensive or unique items, the electron microscope can be applied. The actual anti-counterfeiting medium need not change, only the systems used to check for counterfeiting, though characteristics of the material such as dilution can be changed to allow for customization.

Figure 3:
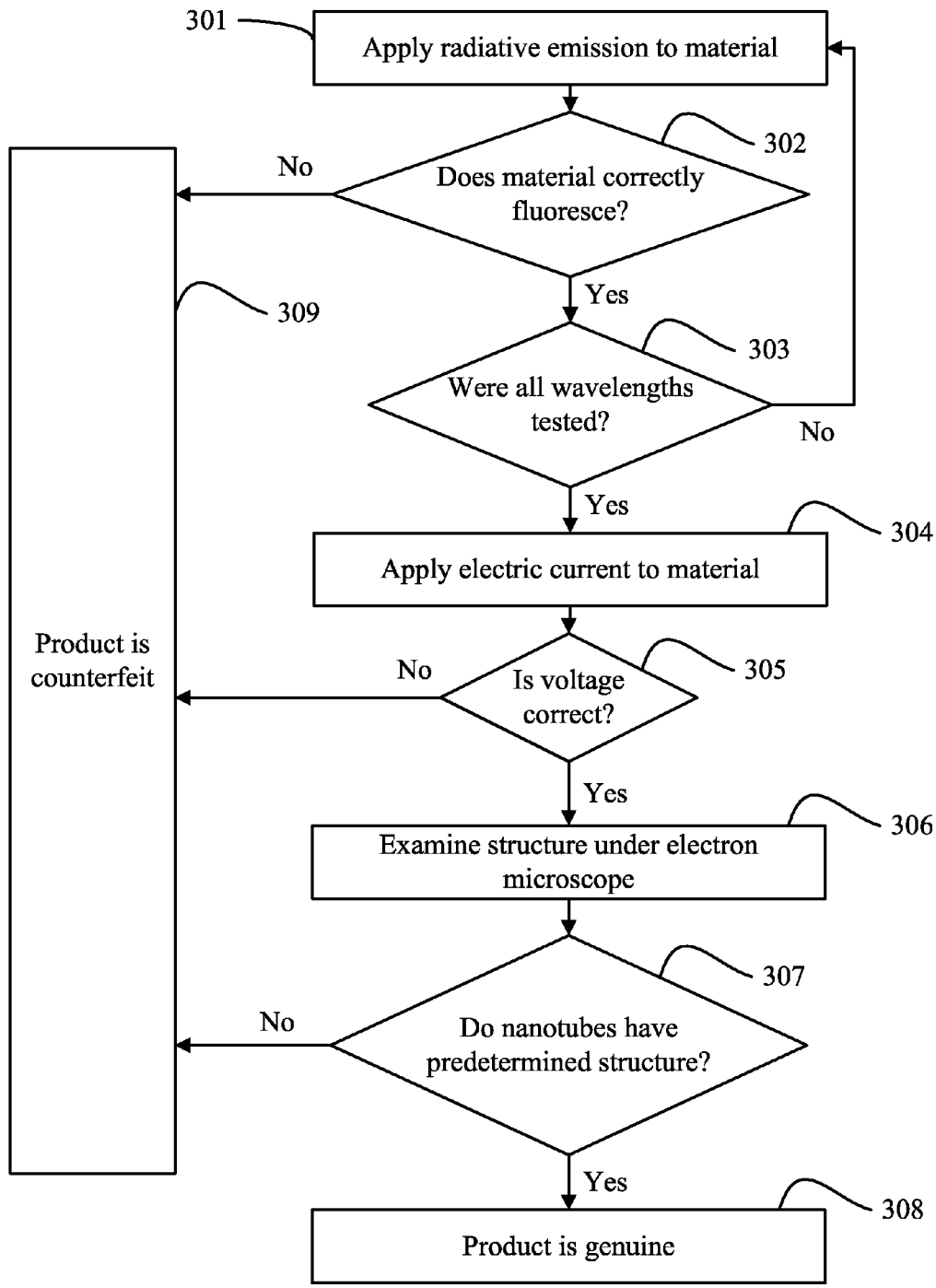
FIG. 3 is a flowchart of a process of verifying the authenticity of a product, according to embodiments of the invention.

FIG. 3 depicts an exemplary method for determining whether a product is authentic according to embodiments of the invention. In 301, a product having a material is exposed to incident radiation. In 302, fluorescence may be checked at a first predetermined wavelength; if the material does not fluoresce at the correct wavelength, then it may be determined that the product is not authentic, i.e., counterfeit, as in 309. If the material does fluoresce at the correct wavelength, it may be determined that the product is authentic. Alternatively, in operation 302, it may be determined if the material fluoresces at a first predetermined wavelength and at a first predetermined intensity. If the material does not fluoresce at the correct wavelength and intensity, then it may be determined that the product is not authentic. If the material does fluoresce at the correct wavelength and intensity, it may be determined that the product is authentic. Operation 302 may only include checking fluorescence at a first predetermined wavelength. Optionally, however, the operation 302 may include checking fluorescence at two or more predetermined wavelengths. In this embodiment, the test may be repeated until all wavelengths have been tested, as in 303. For example, operation 302 may include checking fluorescence at first and second predetermined wavelengths. If the material fluoresces at the first and second predetermined wavelengths, it may be determined that the product is authentic. On the other hand, if the material does not fluoresce at both wavelengths, then it may be determined that the product is not authentic. In one embodiment, a method for determining whether a product is authentic may terminate with operation 303. Alternatively, one or more additional tests may be performed.

In one embodiment, an additional test is performed in operation 304. In operation 304, an electric current may be applied to the material, and checked in 305 to determine whether an expected conductance or resistance is measured. If the measured conductance or resistance is not as expected, it may be determined that the product is not authentic, as in 309. If the measured conductance or resistance is as expected, then it may be determined that the product is authentic. Operations 304 and 305 may be performed alone to determine the authenticity of a product. Alternatively, the operations 304 and 305 may be performed together with another test described herein to determine the authenticity of a product. In one embodiment, a method for determining whether a product is authentic may terminate with operation 305. Alternatively, one or more additional test may be performed.

In one embodiment, the structure of the carbon nanotubes in the material may be examined using electron microscopy, as in 306. Operation 306 may include inspecting the size or shape or other structural characteristic of the carbon nanotubes in a material and comparing an observation with an expected or "controlled for" size or shape of the carbon nanotubes. In operation 307, it may be determine if the observed structural characteristic is substantially the same as the expected structural characteristic. If the expected structure is not observed, then it may be determined that the article is not authentic, as in 309. If the expected structure is observed, then it may be determined that the product is genuine, as in 308.

Experimental Protocols

The following illustrative experimental protocols are prophetic examples which may be practiced in a laboratory environment.

1. Surfactant Production 10 g of phthalocyanine-tetrasulfonic acid nickel(II) complex tetrasodium salt and 1 mL of stearyl alcohol, or about a 4:1 dye to alcohol stoichiometric ratio, are added to a 10 mL solution of 0.1 M N,N-diethylethamine and distilled water in a 20 mL beaker to create a mixture. The mixture is stirred for 1 hr.

2. Surfactant Adsorption and Carbon Nanotube Dispersion

In a 20 mL beaker, 10 mg of single-walled carbon nanotubes are dispersed into 10 mL of a surfactant solution containing 5 g/L of decyl-substituted phthalocyanine-tetrasulfonic acid nickel(II) complex in distilled water. The resulting mixture is sonicated for 1 hr and centrifuged for 10 minutes at 5000 rpm.

What is claimed is:

1. A fluorescent material, comprising:
a medium;
carbon nanotubes dispersed in the medium; and
a first fluorescent surfactant, wherein the first fluorescent surfactant is adsorbed to a surface of a first quantity of the carbon nanotubes in a concentration sufficient to make the material fluoresce in the presence of radiation.

2. The fluorescent material of claim 1, wherein the carbon nanotubes are dispersed in a concentration sufficient to make the material electrically conductive at or above the material's electrical percolation threshold.

3. The fluorescent material of claim 1, wherein the first fluorescent surfactant is in a concentration at or above the first fluorescent surfactant's critical micelle concentration.

4. The fluorescent material of claim 1, wherein the medium is aqueous.

5. The fluorescent material of claim 1, wherein the first fluorescent surfactant fluoresces at a first emission wavelength less than 780 nm.

6. The fluorescent material of claim 5, further comprising a second fluorescent surfactant adsorbed to a second quantity of the carbon nanotubes in a concentration sufficient to make the material fluoresce in the presence of radiation, wherein the second fluorescent surfactant fluoresces at a second emission wavelength in or below the visible spectrum, and the first and second emission wavelengths are different wavelengths.

7. A method for producing a fluorescent material, comprising:
providing a medium;
dispersing carbon nanotubes in the medium; and
adsorbing a first fluorescent surfactant to a first quantity of the carbon nanotubes in a concentration sufficient to make the material fluoresce in the presence of radiation.

8. The method of claim 7, wherein the surfactant-coated carbon nanotubes are dispersed at a concentration above the dispersion's electrical percolation threshold.

9. The method of claim 7, wherein the first fluorescent surfactant is dispersed to a concentration above the first fluorescent surfactant's critical micelle concentration.

10. The method of claim 7, wherein the medium is aqueous.

11. The method of claim 7, wherein the first fluorescent surfactant fluoresces at a first emission wavelength less than 780 nm.

12. The method of claim 11, further comprising adsorbing a second fluorescent surfactant to a second quantity of the carbon nanotubes in a concentration sufficient to make the material fluoresce in the presence of radiation, wherein the second fluorescent surfactant fluoresces at a second emission wavelength in or below the visible spectrum, and the first and second emission wavelengths are different wavelengths.

13. A method for verifying authenticity of a product having a material, comprising:
exposing the material to incident radiation, the material including a medium, carbon nanotubes dispersed in the medium, and a first fluorescent surfactant adsorbed to a first quantity of the carbon nanotubes in a concentration sufficient to make the material fluoresce at a first emission wavelength in the presence of radiation; and
detecting emissive radiation having a first emission wavelength to verify the authenticity of the product.

14. The method of claim 13, wherein the first emission wavelength is in or below the visible spectrum.

15. The method of claim 13, wherein:
the material further includes a second fluorescent surfactant adsorbed to a second quantity of the carbon nanotubes in a concentration sufficient to make the material fluoresce at a second emission wavelength in the presence of radiation, and wherein the second fluorescent surfactant fluoresces at a second emission wavelength in or below the visible spectrum, and the first and second emission wavelengths are different wavelengths; and
the method further comprises detecting emissive radiation having the second emission wavelength to verify the authenticity of the product.

16. The method of claim 13, further comprising:
detecting if the material fluoresces at a first predetermined intensity to verify the authenticity of the product.

17. The method of claim 13, wherein the carbon nanotubes are dispersed in the medium in a concentration sufficient to make the material electrically conductive at or above the material's electrical percolation threshold.

18. The method of claim 17, further comprising testing the electrical conductivity of the material to verify the authenticity of the product.

19. The method of claim 13, further comprising inspecting the material using electron microscopy to determine the presence of a structural characteristic of the carbon nanotubes to verify the authenticity of the product.

* * * * *